US00PP32233P3

(12) United States Plant Patent
Hartman

(10) Patent No.: US PP32,233 P3
(45) Date of Patent: Sep. 22, 2020

(54) ***CALADIUM* PLANT NAMED 'ICE 2319-293'**

(50) Latin Name: ***Caladium* x *hortulanum***
Varietal Denomination: ICE 2319-293

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/501,044

(22) Filed: Feb. 13, 2019

(65) Prior Publication Data

US 2020/0260629 P1 Aug. 13, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

*Primary Examiner* — Anne Marie Grunberg
(74) *Attorney, Agent, or Firm* — C. A. Whealy

(57) ABSTRACT

A new and distinct cultivar of *Caladium* plant named 'ICE 2319-293', characterized by its intermediate height; mounding habit; dense and bushy appearance; vigorous growth habit and rapid growth rate; lance-type leaves that are variegated with a mosaic of irregularly-shaped random sectors that are dark green, medium green, light green, yellow green, greyed green and white in color; and leaf petioles that are dark brown in color with light greyed orange tinged with green-colored stripes and streaks.

5 Drawing Sheets

Figure 1:
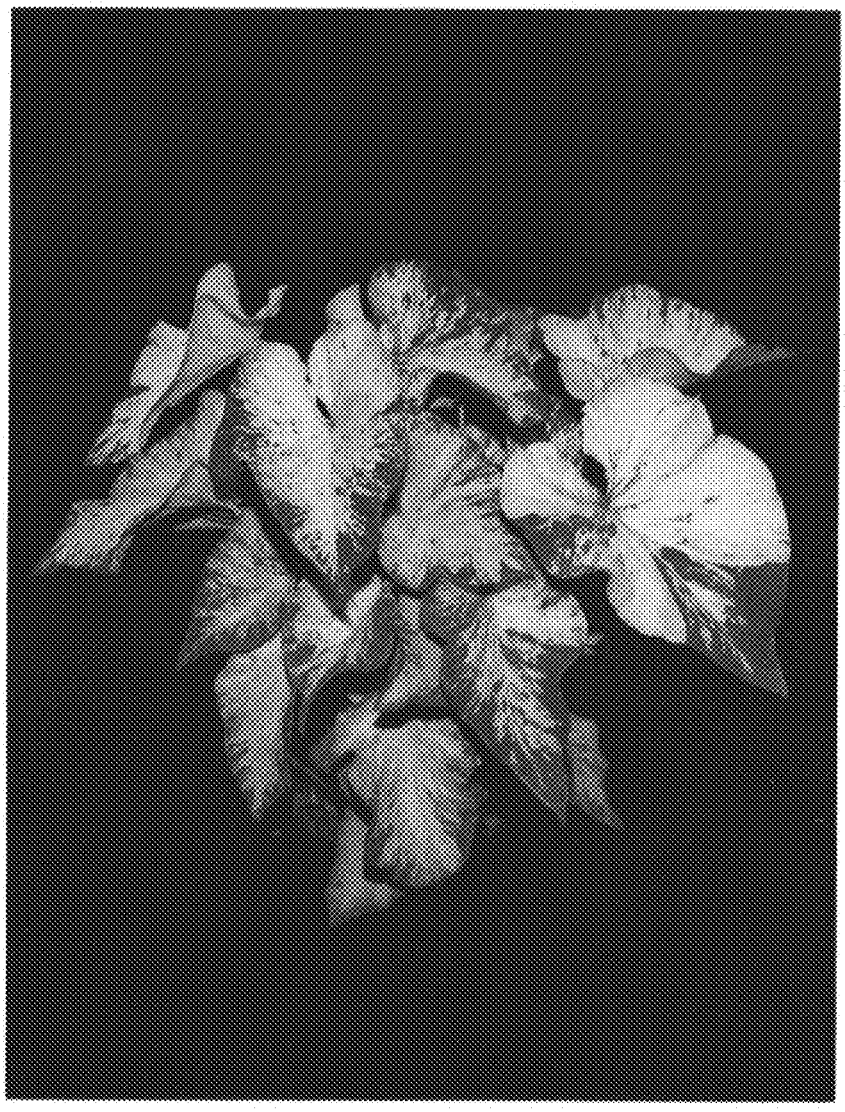

Botanical designation: *Caladium* x *hortulanum*.
Cultivar denomination: 'ICE 2319-293'.

BACKGROUND OF THE INVENTION

The present invention relates to a new and distinct cultivar of *Caladium* plant, botanically known as *Caladium* x *hortulanum*, commercially referred to as a fancy leaf-type *Caladium* and hereinafter referred to by the name 'ICE 2319-293'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium* x *hortulanum* 'White Wonder', disclosed in U.S. Plant Pat. No. 21,044, as the female, or seed, parent with *Caladium* x *hortulanum* 'Highlighter', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2010.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ICE 2319-293'. These characteristics in combination distinguish 'ICE 2319-293' as a new and distinct *Caladium* plant:

1. Intermediate in height and mounding habit; dense and bushy appearance.
2. Vigorous growth habit and rapid growth rate.
3. Lance-type leaves that are variegated with a mosaic of irregularly-shaped random sectors that are dark green, medium green, light green, yellow green, greyed green and white in color.
4. Petioles that are dark brown in color with light greyed orange tinged with green-colored stripes and streaks.

Plants of the new *Caladium* differ primarily from plants of the female parent, 'White Wonder', in the following characteristics:

1. Plants of the new *Caladium* are taller than plants of 'White Wonder'.
2. Plants of the new *Caladium* and 'White Wonder' differ in leaf color as leaves of plants of the new *Caladium* are variegated with a mosaic of random sectors that are dark green, medium green, light green, yellow green, greyed green and white in color whereas leaves of plants of 'White Wonder' are white to grey-green in color with light pink to white-colored venation and dark green-colored borders.
3. Plants of the new *Caladium* and 'White Wonder' differ in leaf petiole color as leaf petioles of plants of the new *Caladium* are dark brown in color with light greyed orange tinged with green-colored stripes and streaks whereas leaf petioles of plants of 'White Wonder' are tan in color with dark brown-colored stripes.

Plants of the new *Caladium* differ primarily from plants of the male parent, 'Highlighter', in the following characteristics:

1. Plants of the new *Caladium* grow faster than plants of 'Highlighter'.
2. Plants of the new *Caladium* and 'Highlighter' differ in leaf color as leaves of plants of the new *Caladium* are variegated with a mosaic of random sectors that are dark green, medium green, light green, yellow green, greyed green and white in color whereas leaves of plants of 'Highlighter' are variegated with random sectors that are light green and dark green in color.
3. Plants of the new *Caladium* and 'Highlighter' differ in leaf petiole color as leaf petioles of plants of the new *Caladium* are dark brown in color with light greyed orange tinged with green-colored stripes and streaks whereas leaf petioles of plants of 'Highlighter' are tan to tan pink in color with diffuse dark brown-colored speckles and streaks.

Plants of the new *Caladium* can be compared to plants of *Caladium* x *hortulanum* 'Heart's Delight', disclosed in U.S. Plant Pat. No. 23,992. In side-by-side comparisons, plants of the new *Caladium* differ primarily from plants of 'Heart's Delight' in the following characteristics:

1. Plants of the new *Caladium* grow faster than plants of 'Heart's Delight'.
2. Plants of the new *Caladium* and 'Heart's Delight' differ in leaf color as leaves of plants of the new *Caladium* are variegated with a mosaic of random sectors that are dark green, medium green, light green, yellow green, greyed green and white in color whereas leaves of plants of 'Heart's Delight' have red-colored venation, greyed purple-colored interveinal areas and mottled light and dark green-colored borders.

Plants of the new *Caladium* can also be compared to plants of *Caladium* x *hortulanum* 'RS-03-03', disclosed in U.S. Plant Pat. No. 26,265. In side-by-side comparisons, plants of the new *Caladium* differ primarily from plants of 'RS-03-03' in the following characteristics:

1. Plants of the new *Caladium* are taller than plants of 'RS-03-03'.
2. Plants of the new *Caladium* and 'RS-03-03' differ in leaf color as leaves of plants of the new *Caladium* are variegated with a mosaic of random sectors that are dark green, medium green, light green, yellow green, greyed green and white in color whereas leaves of plants of 'RS-03-03' are pearlescent white to greenish white in color with dark green-colored margins and white to greenish white-colored venation.
3. Plants of the new *Caladium* and 'RS-03-03' differ in leaf petiole color as leaf petioles of plants of the new *Caladium* are dark brown in color with light greyed orange tinged with green-colored stripes and streaks whereas leaf petioles of plants of 'RS-03-03' are green to tan green in color tinged with brownish green.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 7) is a side perspective view of a typical plant of 'ICE 2319-293' in a container and grown in a shadehouse (tuber de-eyed).

Figure 2:
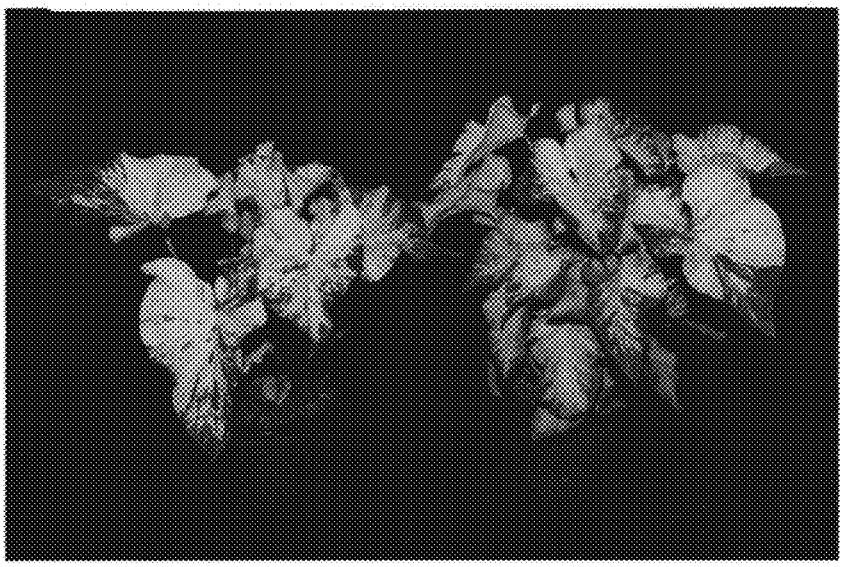

The photograph at the top of the second sheet (FIG. 2 of 7) is a comparison view of typical plants of 'ICE 2319-293' grown in containers; the plant on the left has not had its tuber de-eyed and the plant on the right has had its tuber de-eyed prior to planting.

Figure 3:
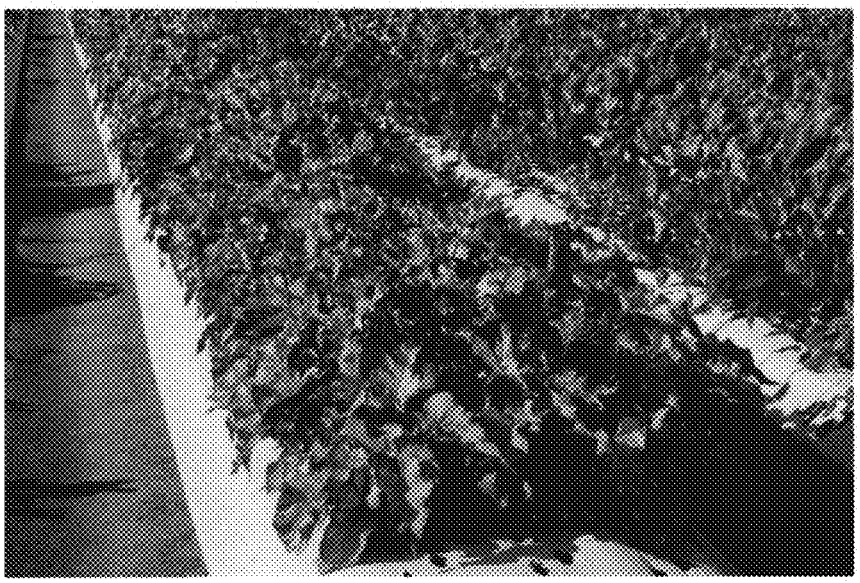

The photograph at the bottom of the second sheet (FIG. 3 of 7) is a side perspective view of typical plants of 'ICE 2319-293' grown in an open production field.

Figure 4:
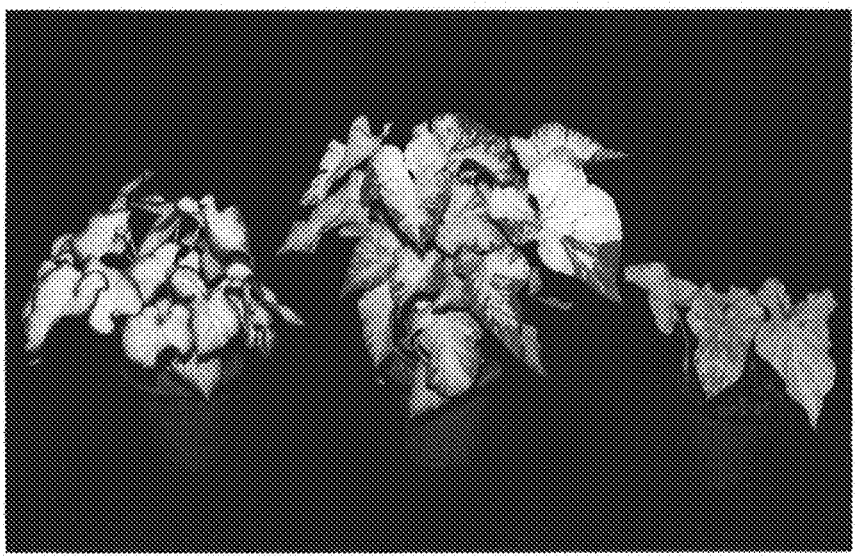

The photograph at the top of the third sheet (FIG. 4 of 7) is a comparison view of typical potted plants of the female parent, 'White Wonder' (left), 'ICE 2319-293' (center) and the male parent, 'Highlighter' (right).

Figure 5:
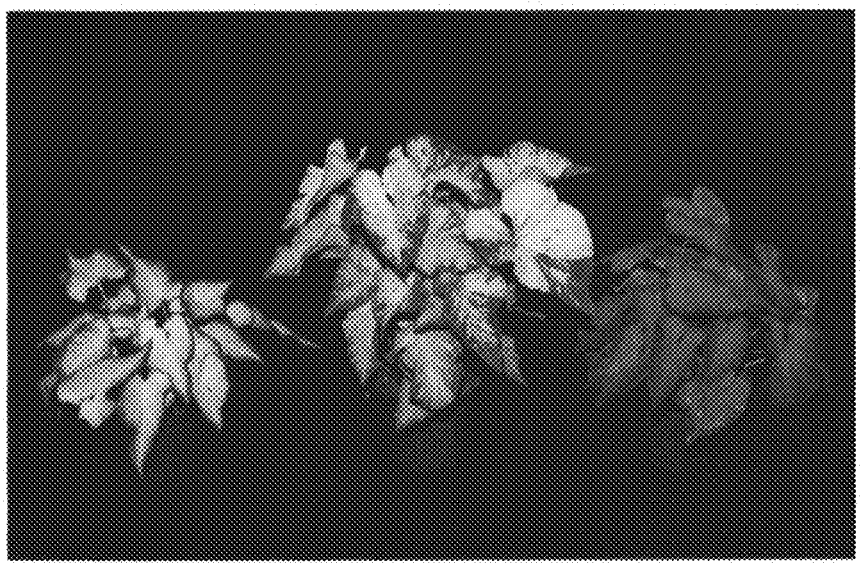

The photograph at the bottom of the third sheet (FIG. 5 of 7) is a comparison view of typical potted plants of 'Heart's Delight' (right), 'ICE 2319-293' (center) and 'RS-03-03' (left).

Figure 6:
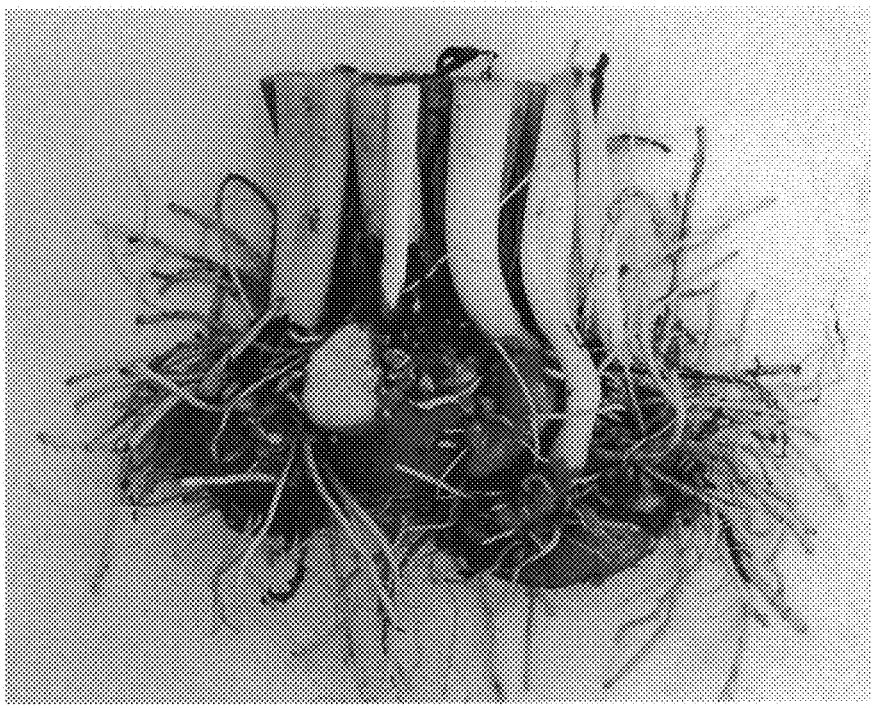

The photograph on the fourth sheet (FIG. 6 of 7) is a close-up view of typical freshly-harvested tubers with roots and leaf petioles of 'ICE 2319-293'.

Figure 7:
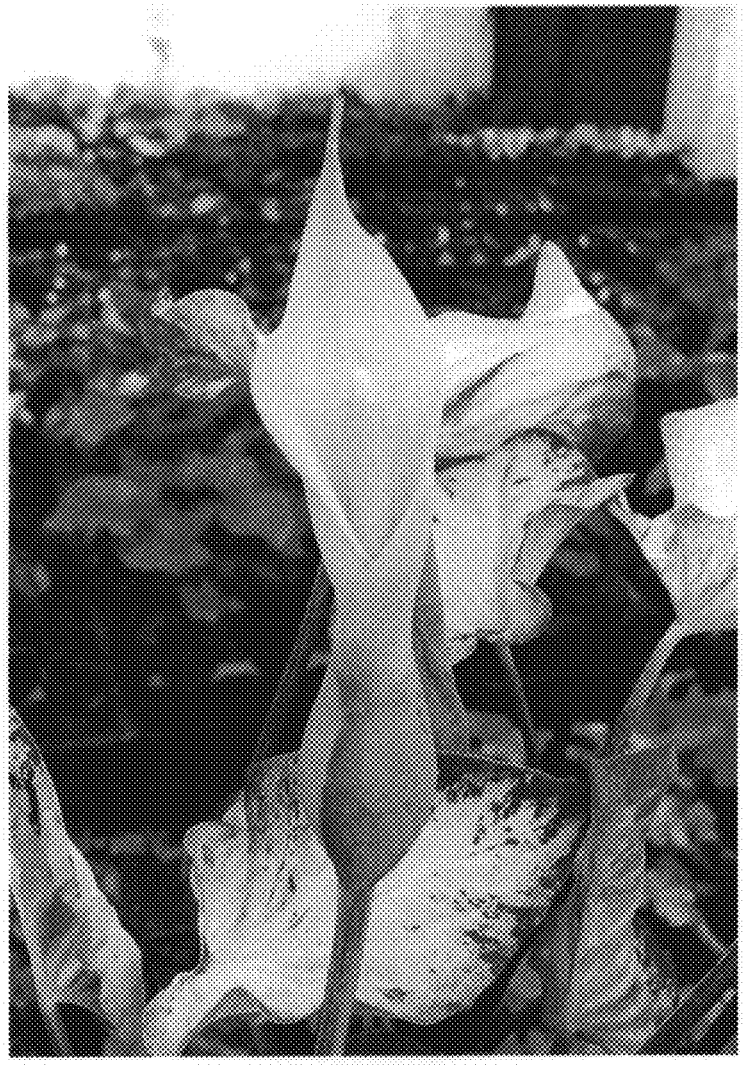

The photograph on the fifth sheet (FIG. 7 of 7) is a close-up view of a typical inflorescence of 'ICE 2319-293'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* x *hortulanum* 'ICE 2319-293'.

Parentage:

*Female, or seed, parent.*—*Caladium* x *hortulanum* 'White Wonder', disclosed in U.S. Plant Pat. No. 21,044.

*Male, or pollen, parent.*—*Caladium* x *hortulanum* 'Highlighter', not patented.

Propagation:

*Type.*—By "chipping" the tubers.

*Time to initiate roots, summer.*—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments elliptic to round in shape. Height: About 3.5 cm. Diameter: About 5 cm to 9.3 cm. Segment height: About 2 cm. Segment diameter: About 2 cm. Axillary bud size: About 4 mm by 4 mm. Texture: Thick, starchy; somewhat brittle. Color: Epidermis, freshly-harvested: Close to 173D and 179D. Epidermis, dried: Close to 200A. Cortical tissue: Close to 5C. Axillary buds: Close to 39C. Root description: Thick, fleshy contractile roots with few lateral branches; color, close to N155D tinged with 63D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate in height and mounded plant habit; inverted triangle and wider than tall; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and leaning and arching outwardly with development.

*Plant height, from soil level to top of foliar plane, shadehouse-grown potted plants*.—About 25 cm to 29 cm.

*Plant height, from soil level to top of inflorescences, shadehouse-grown potted plants*.—About 26.5 cm.

*Plant diameter or spread, shadehouse-grown potted plants*.—About 38 cm to 45 cm.

*Number of shoots per plant, shadehouse-grown potted plants, tubers not de-eyed*.—About three to four develop per #1 tuber.

*Number of shoots per plant, shadehouse-grown potted plants, tubers de-eyed*.—About four to five develop per #1 tuber.

*Cataphylls, shadehouse-grown potted plants*.—Length: About 4.7 cm to 7.7 cm. Width: About 1.5 cm. Shape: Narrowly elliptic. Apex: Acute. Base: Sheathing the stem. Color, inner surface: Close to 155C; colors and patterns on the outer surface are visible on the inner surface. Color, outer surface: Close to N170D and 195D densely streaked, stippled and striped with 200A; with development, color becoming closer to N200A stained with N186C.

Leaf description:

*Arrangement and type*.—Alternate; simple; lance-type.

*Length, shadehouse-grown potted plants*.—About 14 cm to 18 cm.

*Width, shadehouse-grown potted plants*.—About 9.2 cm to 11.5 cm; when flattened, about 9.5 cm to 12 cm.

*Shape*.—Ovate to lanceolate.

*Apex*.—Acuminate.

*Base*.—Sagittate to peltate.

*Margin*.—Entire; wavy with broad undulations.

*Texture and luster, upper surface*.—Smooth, glabrous; dull sheen.

*Texture and luster, lower surface*.—Smooth, glabous; slightly glaucous; dull sheen.

*Venation pattern*.—Pinnate.

*Color, shadehouse-grown potted plants*.—Developing and fully developed leaves, upper surface: Lamina: Variegated with a mosaic of random and irregularly-shaped sectors that are close to darker than 147A, 147A, 147B, 147C, 137A, 137B, 137C, 145C, 145D, 194A, 194B and 155A. Leaf edge: Close to 187A or similar to lamina colors. Basal notch: Close to 187A and 185A. Midvein and lateral venation: Similar to lamina colors. Developing and fully developed leaves, lower surface: Lamina: Variegated with a mosaic of random and irregular sectors that are close to 147B, 147C, 145D, 191A, 194B, 157B, 157C. Leaf edge: Close to 191A or 187A. Basal notch: Close to 146C faintly tinged with 187B and 183A. Midvein: Close to 147C. Primary venation: Close to 147C to 147D.

*Petioles*.—Aspect: Initially upright and straight and outwardly leaning and arching with development; flexible. Length, shadehouse-grown potted plants: About 15 cm to 21.5 cm. Diameter, distally, shadehouse-grown potted plants: About 3.5 mm to 4 mm. Diameter, proximally, shadehouse-grown potted plants: About 6 mm to 7.5 mm. Texture and luster: Smooth, glabrous; glaucous; dull. Color, shadehouse-grown potted plants, when developing and fully developed: Proximally, close to 200A striped and streaked with N170D or close to N170D tinged with 147B and streaked, stippled and striped with 200A to 200B tinged with 147B; distally (just below leaf junction), similar to proximal colors or close to 147C to 147D streaked, stippled and striped with 200B to 200C. Wing length, shadehouse-grown potted plants: About 3.2 cm to 4.5 cm. Wing diameter, shadehouse-grown potted plants: About 7 mm. Texture and luster, inner and outer surfaces: Smooth, glabrous; dull to slightly glossy. Wing color, shadehouse-grown potted plants: Inner surface: Close to N155C; colors and patterns on the outer surface are visible on the inner surface. Outer surface: Close to N170D and 195D densely streaked and striped with 200B tinged with 147B.

Inflorescence description: Inflorescences observed on seven week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; camphor with jasmine-like notes.

*Natural flowering season and flower longevity*.—Plants of the new *Caladium* typically flower during the spring in central Florida; flowers develop about seven weeks after growth commences; inflorescences last about three days before fading; inflorescences persistent.

*Spathe*.—Length, overall: About 11.5 cm. Length, distal open portion: About 8.5 cm. Length, proximal closed portion: About 3 cm. Width, distal open portion: About 2.6 cm. Depth, distal open portion: About 2.2 cm. Width, at constriction: About 1.5 cm. Width, proximal closed portion: About 2.2 cm. Shape, open portion: Narrowly elliptic. Apex: Acute. Base: Acute. Margin: Entire; smooth. Texture and luster, front surface: Smooth, glabrous; dull. Texture and luster, rear surface: Smooth, glabrous; dull; proximally, slightly glaucous. Color, front surface: Distal open portion: Close to 150D; towards the margins, close to 155C; with development, color becoming closer to 199A. Proximal closed portion: Close to 147D; color does not change with development. Color, rear surface: Distal open portion: Close to 154D, 147D and 146D; color does not change with development. Proximal closed portion: Close to 147B, 148C and 147C tinged with 146C; color does not change with development.

*Spadix*.—Length, overall: About 7 cm. Length, male flower zone: About 4.1 cm. Length, sterile zone: About 1.4 cm. Length, female flower zone: About 1.5 cm. Diameter, male flower zone: About 8 mm. Diameter, sterile flower zone: About 5 mm. Diameter, female flower zone: About 9 mm. Shape: Spindle-shaped. Apex: Acute. Base: Truncate. Aspect: Upright. Color, mature, male zone: Close to 159D. Color, mature, sterile zone: Close to N155C. Color, mature, female zone: Close to 159C. Male flowers: Quantity per spadix: About 100. Shape: Obovate. Height: About 2.2 mm. Diameter: About 2.8 mm. Pollen amount: Moderate. Pollen color: Close to 10C to 10D. Female flowers: Quantity per spadix: About 180. Shape: Obovate. Height: About 2.2 mm. Diameter: About 1.8 mm. Stigma color: Close to 159C. Ovary color: Close to N170D and 181B.

*Scape*.—Length: About 15 cm. Diameter: About 5.5 mm. Strength: Sturdy; flexible. Aspect: Mostly erect. Texture and luster: Smooth, glabrous; slightly glossy. Color: Close to 147C stippled, streaked and striped with 200A and N200A; distally, close to 147B and 146C or close to 146B to 146C.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'ICE 2319-293' as illustrated and described.

* * * * *